US011199502B2

(12) United States Patent
Song et al.

(10) Patent No.: US 11,199,502 B2
(45) Date of Patent: Dec. 14, 2021

(54) FULLY VISUAL FLOW LOOP SYSTEM FOR STUDYING HYDRATE BLOCKAGE

(71) Applicant: Dalian University of Technology, Dalian (CN)

(72) Inventors: Yongchen Song, Dalian (CN); Jiafei Zhao, Dalian (CN); Zheyuan Liu, Dalian (CN); Weiguo Liu, Dalian (CN); Yu Liu, Dalian (CN); Huiyong Liang, Dalian (CN); Jiawei Chu, Dalian (CN); Mingjun Yang, Dalian (CN); Yanghui Li, Dalian (CN)

(73) Assignee: Dalian University of Technology, Dalian (CN)

( * ) Notice: Subject to any disclaimer, the term of this patent is extended or adjusted under 35 U.S.C. 154(b) by 643 days.

(21) Appl. No.: 16/195,134

(22) Filed: Nov. 19, 2018

(65) Prior Publication Data

US 2020/0096452 A1    Mar. 26, 2020

(30) Foreign Application Priority Data

Sep. 21, 2018 (CN) .......................... 201811104139.5

(51) Int. Cl.
*G01N 21/85* (2006.01)
*F04D 3/02* (2006.01)
(Continued)

(52) U.S. Cl.
CPC .............. *G01N 21/85* (2013.01); *F04D 3/02* (2013.01); *F16L 9/105* (2013.01); *F17D 1/02* (2013.01);
(Continued)

(58) Field of Classification Search
CPC .... G01N 17/002; G01N 17/004; G01N 21/85; G01N 21/01; G01N 21/75; G01N 33/22;
(Continued)

(56) References Cited

U.S. PATENT DOCUMENTS 4,512,280 A * 4/1985 Lee, Jr. .................. B65G 25/08
118/426
5,147,136 A * 9/1992 Hartley ..................... B01L 1/02
374/57
(Continued)

*Primary Examiner* — Peter J Macchiarolo
*Assistant Examiner* — Mohammed E Keramet-Amircolai
(74) *Attorney, Agent, or Firm* — Garvey, Smith & Nehrbass, Patent Attorneys, L.L.C.; Vanessa M. D'Souza; Seth M. Nehrbass

(57) ABSTRACT

The present invention discloses a fully visual flow loop system for studying hydrate blockage. The fully visual flow loop system includes a first pipeline, a second pipeline, a third pipeline and a fourth pipeline connected successively in an end-to-end way; a single screw pump is connected between the first pipeline and the fourth pipeline from the four pipelines; the first pipeline, the second pipeline, the third pipeline and the fourth pipeline are all transparent to light; a plurality of CCD cameras are arranged between the first pipeline, the second pipeline, the third pipeline and the fourth pipeline; and, the fully visual flow loop system is arranged in a stepping low-temperature thermostatic chamber; a solution injection system can inject a solution into the fully visual flow loop system; a separation and collection system can separate and recover the solution; and a data acquisition system can integrate sensor information in all the other systems and give real-time feedback to ensure reasonable and coordinated operation of all systems. The fully visual flow loop system for studying hydrate blockage in the present invention can realize full visualization and real-time monitoring of the flow loop system.

20 Claims, 4 Drawing Sheets

(51) Int. Cl.
*F16L 9/10* (2006.01)
*F17D 1/02* (2006.01)
*G01M 99/00* (2011.01)
*G01N 21/01* (2006.01)
*G01N 21/75* (2006.01)
*G01N 33/22* (2006.01)

(52) U.S. Cl.
CPC ............ *G01M 99/00* (2013.01); *G01N 21/01* (2013.01); *G01N 21/75* (2013.01); *G01N 33/225* (2013.01)

(58) Field of Classification Search
CPC ...... H01L 2924/00014; G01M 99/002; G01M 99/00; G01R 31/2849; F04D 3/02; F16L 9/10; F17D 1/02
USPC ...................................................... 73/865.6
See application file for complete search history.

(56) References Cited

U.S. PATENT DOCUMENTS

| | | | | |
|---|---|---|---|---|
| 5,267,467 | A * | 12/1993 | Caron | G01F 1/36 73/1.26 |
| 5,503,032 | A * | 4/1996 | Tikhtman | G01N 17/00 165/247 |
| 2004/0149054 | A1* | 8/2004 | Soga | G01N 17/002 73/865.6 |
| 2012/0297904 | A1* | 11/2012 | Pickel | G01M 99/002 73/865.6 |
| 2017/0350290 | A1* | 12/2017 | Yang | F01N 9/00 |
| 2019/0039916 | A1* | 2/2019 | Song | C10L 3/104 |
| 2021/0003517 | A1* | 1/2021 | Song | G01N 23/046 |

\* cited by examiner

FULLY VISUAL FLOW LOOP SYSTEM FOR STUDYING HYDRATE BLOCKAGE

This application claims priority to Chinese patent application number 201811104139.5, filed on 21 Sep. 2018, with a title of FULLY VISUAL FLOW LOOP SYSTEM FOR STUDYING HYDRATE BLOCKAGE. The above-mentioned patent application is incorporated herein by reference in its entirety.

TECHNICAL FIELD

The present invention relates to the technical field of pipeline flow assurance control, in particular to a fully visual flow loop system for studying hydrate blockage.

BACKGROUND

Hydrocarbon molecules in natural gas combine with free water under certain temperature and pressure conditions to form a natural gas hydrate, and the natural gas hydrate is a white crystalline solid. It is very easy to produce the natural gas hydrate in the oil and gas exploitation and transportation process especially in low-temperature and high-pressure deep water environments, and the natural gas hydrate will block a conveying pipeline. It is very difficult to clear the natural gas hydrate in the pipeline in deep water environment, which seriously affects the oil and gas exploitation efficiency. The study of the flow assurance problem caused by the natural gas hydrate in the pipeline is helpful to solve the above problem.

The existing flow assurance experiments of flow loops can realize a certain degree of scientific research and acquire relevant experimental data, but full visualization is not realized. Neither can the blockage state of natural gas hydrate state in the pipeline be entirely observed, nor real-time images for blockage process of hydrate can be obtained, and basic data cannot be provided for the solution of the flow assurance problem in the seabed oil and gas pipeline transportation process. At present, the injection and discharge system matched with the existing flow loop can only realize a small degree of gas-liquid multiphase injection, and experimental gases and liquids cannot be recycled and may destroy the environment.

SUMMARY

The present invention aims at providing a fully visual flow loop system for studying hydrate blockage in order to solve the problems existing in the prior art and realize full visualization and real-time monitoring of the flow loop system.

To achieve the above objective, the present invention provides: a fully visual flow loop system for studying hydrate blockage, including a fully visual pipeline system, a solution injection system, a separation and collection system and a data acquisition system; where
the fully visual pipeline system includes a single screw pump and a first pipeline, a second pipeline, a third pipeline and a fourth pipeline connected successively in an end-to-end way; where the single screw pump is connected between the first pipeline and the fourth pipeline; the first pipeline, the second pipeline, the third pipeline and the fourth pipeline are transparent to light; a plurality of charge-coupled device (CCD) cameras are arranged among the first pipeline, the second pipeline, the third pipeline and the fourth pipeline; the fully visual pipeline system is arranged in a stepping low-temperature thermostatic chamber; and a heat exchanger is arranged at one side of the stepping low-temperature thermostatic chamber;
the solution injection system includes a first solution tank and a second solution tank, where the first solution tank communicates with the single screw pump through a first solution conveying pipe, the second solution tank communicates with the single screw pump through a second solution conveying pipe, reciprocating pumps are arranged on the first solution tank and the second solution tank respectively, and a liquid flowmeter is also arranged on the first solution conveying pipe;
the separation and collection system includes a natural gas collection tank connected with the fully visual pipeline system, where a gas-liquid separator and a burner are connected to an outlet of the natural gas collection tank;
the data acquisition system includes: pressure sensors arranged on the first solution conveying pipe, the second solution conveying pipe, the first pipeline, the second pipeline, the third pipeline and the fourth pipeline; temperature sensors arranged on the first pipeline, the second pipeline, the third pipeline and the fourth pipeline; a plurality of CCD cameras arranged between the first pipeline, the second pipeline, the third pipeline and the fourth pipeline; and a computer electrically connected with the CCD cameras, the pressure sensors and the temperature sensors, respectively.

Optionally, the first pipeline, the second pipeline, the third pipeline and the fourth pipeline are arranged horizontally and successively in parallel; the first pipeline, the second pipeline, the third pipeline and the fourth pipeline are connected successively through stainless steel bent pipes; the first pipeline also communicates with an inlet of the single screw pump through a first injection pipeline; the fourth pipeline also communicates with an outlet of the single screw pump through a second injection pipeline; a mass flowmeter is connected to the outlet of the single screw pump; the first injection pipeline is connected with the second injection pipeline through a connecting pipe; and a differential pressure sensor and a first pneumatic valve are arranged on the connecting pipe; the first pipeline, the second pipeline, the third pipeline and the fourth pipeline are all formed by connecting a plurality of organic glass straight pipes; the stainless steel bent pipes and the organic glass straight pipes are all made of high-transparency materials; and an acoustic wave monitor, a gate valve and a ball valve are arranged on the first pipeline.

Optionally, one end of each visual pipe stretches into sealing flanges A, and support rings, check rings, O-rings A and distance rings installed between the visual pipes and the sealing flanges A in order from inside to outside; flange plates of the two sealing flanges A are fixed and abutted through bolts, a sealing gasket is placed between the flange plates of the two sealing flanges, a distance bush is placed between the visual pipes respectively stretching into the two sealing flanges A, and washers A are installed between the distance bush and the visual pipes; and sensors are placed in sensor interfaces arranged on the sealing flanges A, and the pipeline is entirely fixed on the support through a U-shaped clamp slot.

Optionally, the second pipeline and the third pipeline are both laid on a movable base, where one end of the movable base is rotatably connected to the ground, and the other end of the movable base can be lifted up through a chain block.

Optionally, the solution injection system further includes a vacuum pump connected to the first injection pipeline, where a valve and a pressure sensor electrically connected with the computer are arranged on the pipeline between the vacuum pump and the first injection pipeline.

Optionally, a back pressure control system is arranged between the natural gas collection tank and the fully visual pipeline, where the back pressure control system includes a back pressure regulating valve and a hand shutoff valve arranged between the natural gas collection tank and the fully visual pipeline as well as a pressure sensor connected with the computer.

Optionally, the fully visual flow loop system for studying hydrate blockage further includes a pressure stabilizing and gas injection system; the pressure stabilizing and gas injection system includes a buffering and pressure stabilizing tank, a first gas booster pump and an experimental gas cylinder group successively communicating with each other; the buffering and pressure stabilizing tank communicates with the second injection pipeline, a check valve, a gas flowmeter, a gas filter and a second pneumatic valve arranged on the pipeline between the buffering and pressure stabilizing tank and the second injection pipeline; and the gas flowmeter and the second pneumatic valve are connected with the gas filter in parallel; and the gas-liquid separator communicates with one end of the second gas booster pump, and the other end of the gas booster pump communicates with the natural gas collection tank.

Optionally, a deadleg is arranged on the fourth pipeline.

Optionally, the structure of the deadleg is as follows: one end of a stainless steel tee pipe is connected with a steel pipe sealing flange B, a rotating joint at the other end stretches into a sealing flange C, a support belt, an O-ring D and a U-ring B are arranged between the sealing flange C and the rotating joint, the sealing flange C is abutted with the steel pipe flange, and an O-ring C is arranged on one face of the sealing flange C abutted with the steel pipe flange.

Optionally, a locating plate is arranged on the stainless steel tee pipe, a plurality of locating holes are arranged in the locating plate, a locating rack is arranged on the sealing flange C, a spring pin assembly is arranged on the locating rack, and the spring pin assembly is connected with the locating plate and the locating rack through the locating holes.

Optionally, both ends of a visual short pipe stretch into the top cover flanges respectively, the top cover flange at the lower end is connected with a branch of the stainless steel tee pipe, a drain valve is arranged on the top cover flange at the upper end, the top cover flanges at both ends are permanently connected through a protective pipe, washers are arranged between the end faces of the visual short pipe and the top cover flanges, and O-rings B and U-rings A are arranged between the outer wall of the visual short pipe and the top cover flanges.

Optionally, visual windows are arranged in all of the stainless steel bent pipes, and a drain valve is arranged on one of the stainless steel bent pipes.

Optionally, a methane concentration sensor electrically connected with the computer is also arranged at one side of the stepping low-temperature thermostatic chamber.

Compared with the prior art, the fully visual flow loop system for studying hydrate blockage in the present invention has the following advantages:

The fully visual flow loop system for studying hydrate blockage in the present invention can realize full visualization and real-time monitoring of the flow loop system. The whole fully visual pipeline system is formed of transparent organic glass straight pipes, and CCD cameras can monitor the pipeline state in real-time. The temperature, pressure, flow and acoustic wave signals in hydrate formation are monitored in real-time and analyzed by a data acquisition and analysis system formed of temperature sensors, pressure sensors, a differential pressure sensor, a mass flowmeter, an acoustic wave monitor and a data acquisition system. Real-time images for the hydrate formation process can be obtained through the CCD cameras and the data acquisition system. Comprehensive data and assessment can be provided for the flow assurance problem of seabed oil and gas transportation. The fully visual flow loop system for studying hydrate blockage has the advantages of reasonable structure, ease and convenience in operation, ease in observation, etc. A solution injection system is formed of two solution tanks, namely two sets of solution injection systems, so that the mixed and quantitative injection of two solutions can be realized. The coordination and cooperation between a buffering and pressure stabilizing tank and a pneumatic valve makes natural gas injected into an experimental system stably at constant pressure, and gas can be automatically supplemented through pressure data given by the experimental system. Discharged experimental gas can be recollected through a natural gas collection tank, the gas can be reutilized through a gas booster pump, or the experimental waste gas can be burned up through a burner to prevent greenhouse gases from being discharged into the atmosphere. The fully visual flow loop system for studying hydrate blockage in the present invention can efficiently, stably and eco-friendly provide multiphase fluid injection for the flow loop experiment system and can further provide technical and data support for the flow assurance problem in the deep sea oil and gas pipeline transportation process.

BRIEF DESCRIPTION OF THE DRAWINGS

To describe the technical solutions in preferred embodiments of the present invention or in the prior art more clearly, the following briefly describes the accompanying drawings required for describing preferred embodiments. The accompanying drawings in the following description show some embodiments of the present invention, and a person of ordinary skill in the art may still derive other drawings from these accompanying drawings without creative efforts.

DETAILED DESCRIPTION

The following describes certain preferred embodiments of the present invention with reference to the accompanying drawings. The described preferred embodiments are merely a part, rather than all, of the embodiments of the present invention. All other embodiments obtained by a person of ordinary skill in the art based on the embodiments of the present invention without creative efforts shall fall within the protection scope of the present invention.

The present invention provides a fully visual flow loop system for studying hydrate blockage in order to solve the problems existing in the prior art and realize full visualization and real-time monitoring of the flow loop system.

The present invention will be further illustrated hereinafter in detail in combination with the drawings and preferred embodiments in order to make the above purpose, features and advantages of the present invention more obvious and understandable.

As shown in FIGS. 1-4, the fully visual flow loop system for studying hydrate blockage in the present invention includes a fully visual pipeline system, a solution injection system, a pressure stabilizing and gas injection system, a back pressure control system, a separation and collection system and a data acquisition system 15.

Figure 6:
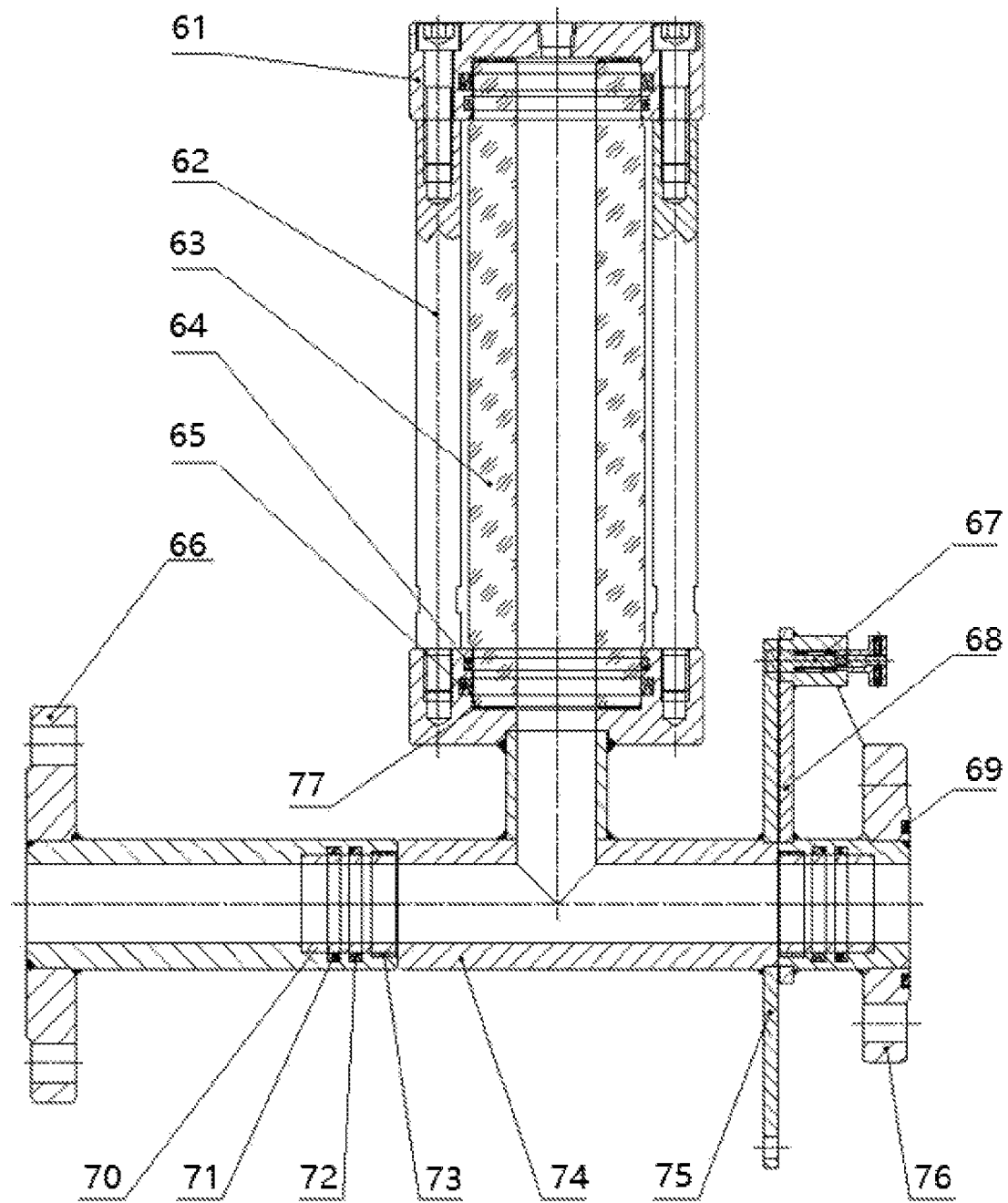
FIG. 6 is a structural diagram of a deadleg in the fully visual flow loop system for studying hydrate blockage in the present invention.

The fully visual pipeline system includes a single screw pump 16 and a first pipeline, a second pipeline, a third pipeline and a fourth pipeline connected successively in an end-to-end way, the first pipeline 78, the second pipeline 79, the third pipeline 80 and the fourth pipeline 81 are arranged horizontally and successively in parallel; one end of the first pipeline is connected with one end of the second pipeline through a stainless steel bent pipe 5, the other end of the second pipeline is connected with one end of the third pipeline through a stainless steel bent pipe 5, the other end of the third pipeline is connected with one end of the fourth pipeline through a stainless steel bent pipe 5, the other end of the first pipeline communicates with an inlet of a single screw pump 16 through a stainless steel bent pipe 5 and a first injection pipeline 18, the other end of the fourth pipeline communicates with an outlet of the single screw pump 16 through a second injection pipeline 39, and a mass flowmeter 13 is also connected to the outlet of the single screw pump 16; the first injection pipeline 18 is connected with the second injection pipeline 39 through a connecting pipe, and a differential pressure sensor 12 and a first pneumatic valve 20 are arranged on the connecting pipe; the second pipeline and the third pipeline in the fully visual pipeline system are laid on a movable base 23, one end of the movable base 23 is connected to the ground, and a chain block 22 can lift the other end of the movable base 23; and the second pipeline and the third pipeline are fluctuating pipelines, connecting hoses 21 are connected to the second pipeline and the third pipeline, the chain block 22 arranged on the movable base 23 can control the fluctuation of the fluctuating pipelines, and a fluctuation angle of 0-15° can be realized. A deadleg 24 is arranged on the fourth pipeline and is used for observing the state of a flow dead zone, and a drain valve 17 is arranged on the stainless steel bent pipe 5 between the third pipeline and the fourth pipeline and can facilitate emptying the gas in the pipelines. The structure of the deadleg is as follows (see FIG. 6): one end of a stainless steel tee pipe 74 is connected with a steel pipe sealing flange B 66, a rotating joint at the other end stretches into a sealing flange C 76, a support belt 73, an O-ring D 72 and a U-ring B 71 are arranged between the sealing flange C 76 and the rotating joint 70, the sealing flange C 76 is abutted with the steel pipe flange, and an O-ring C 69 is arranged on one face of the sealing flange C 76 abutted with the steel pipe flange; a locating plate 75 is arranged on the stainless steel tee pipe 74, a plurality of locating holes are arranged in the locating plate 75, a locating rack 68 is arranged on the sealing flange C 76, a spring pin assembly 67 is arranged on the locating rack 68, and the spring pin assembly 67 is connected with the locating plate 75 and the locating rack 68 through the locating holes; and both ends of a visual short pipe 63 stretch into the top cover flanges 61 respectively, the top cover flange at the lower end is connected with a branch of the stainless steel tee pipe 74, a drain valve is arranged on the top cover flange at the upper end, the top cover flanges at both ends are permanently connected through a protective pipe 62, washers B 77 are arranged between the end faces of the visual short pipe 63 and the top cover flanges 61, and O-rings B 64 and U-rings A 65 are arranged between the outer wall of the visual short pipe and the top cover flanges.

Figure 1:
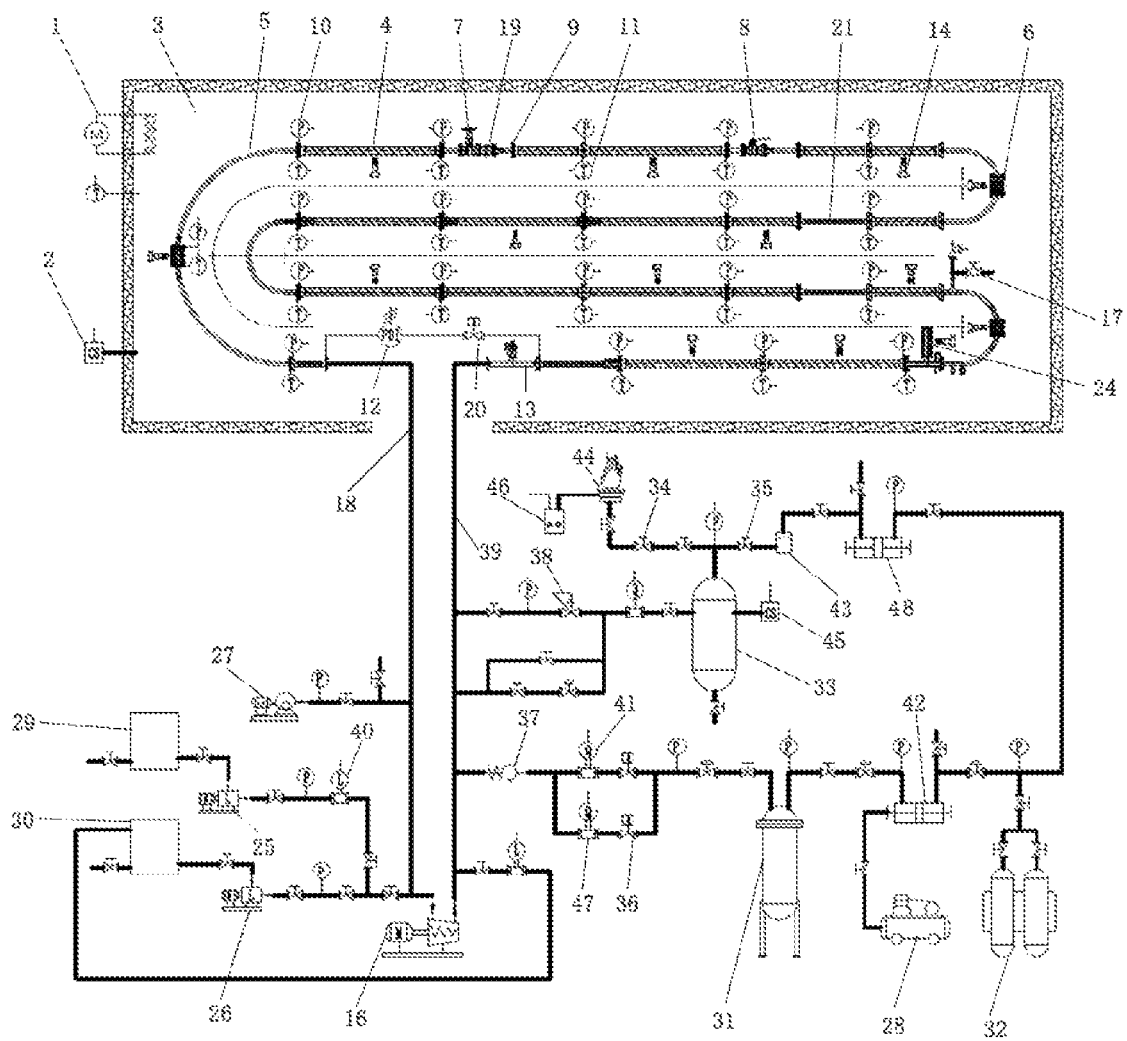
FIG. 1 is a structural diagram of the fully visual flow loop system for studying hydrate blockage in the present invention.
Figure 2:
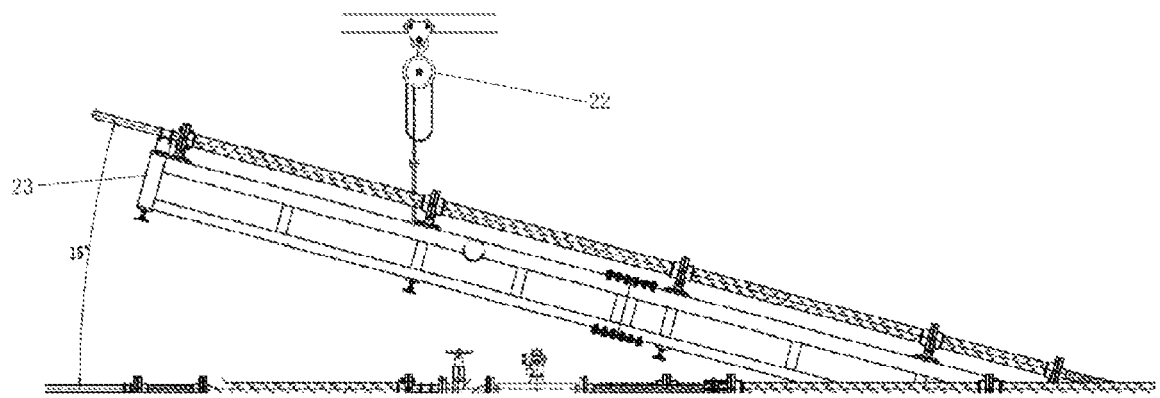
FIG. 2 is a structural diagram of the fully visual pipeline system in the fully visual flow loop system for studying hydrate blockage in the present invention.
Figure 3:
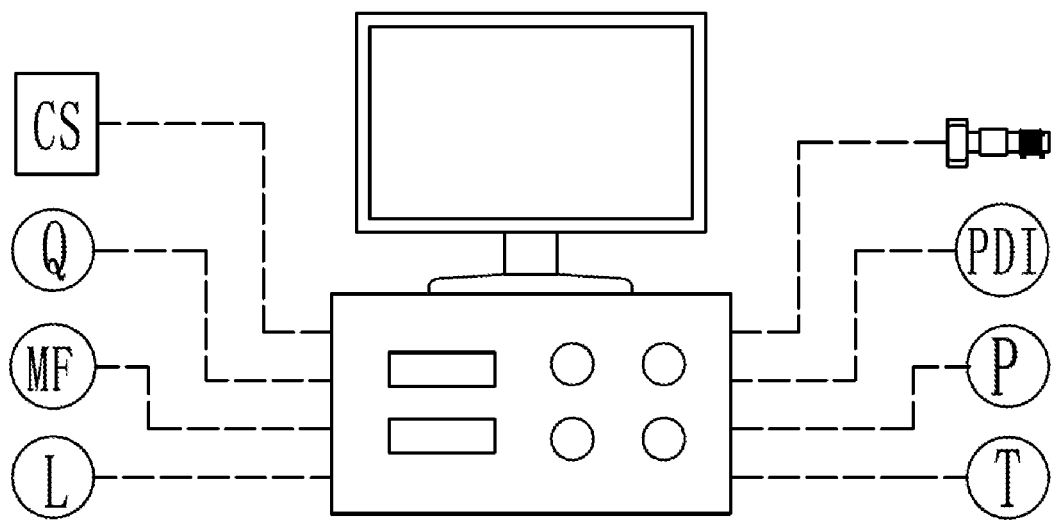
FIG. 3 is a structural diagram of the data acquisition system in the fully visual flow loop system for studying hydrate blockage in the present invention.
Figure 4:
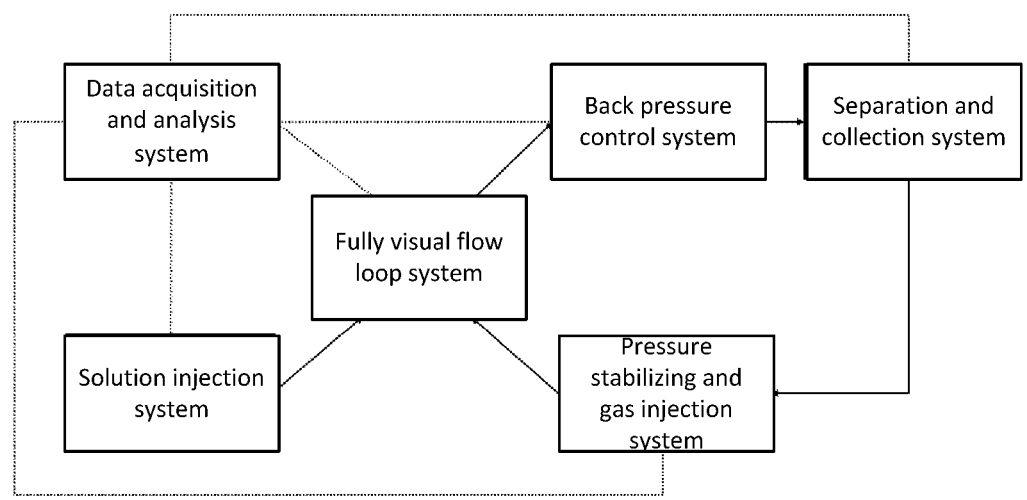
FIG. 4 is a schematic diagram of the fully visual flow loop system for studying hydrate blockage in the present invention.
Figure 5:
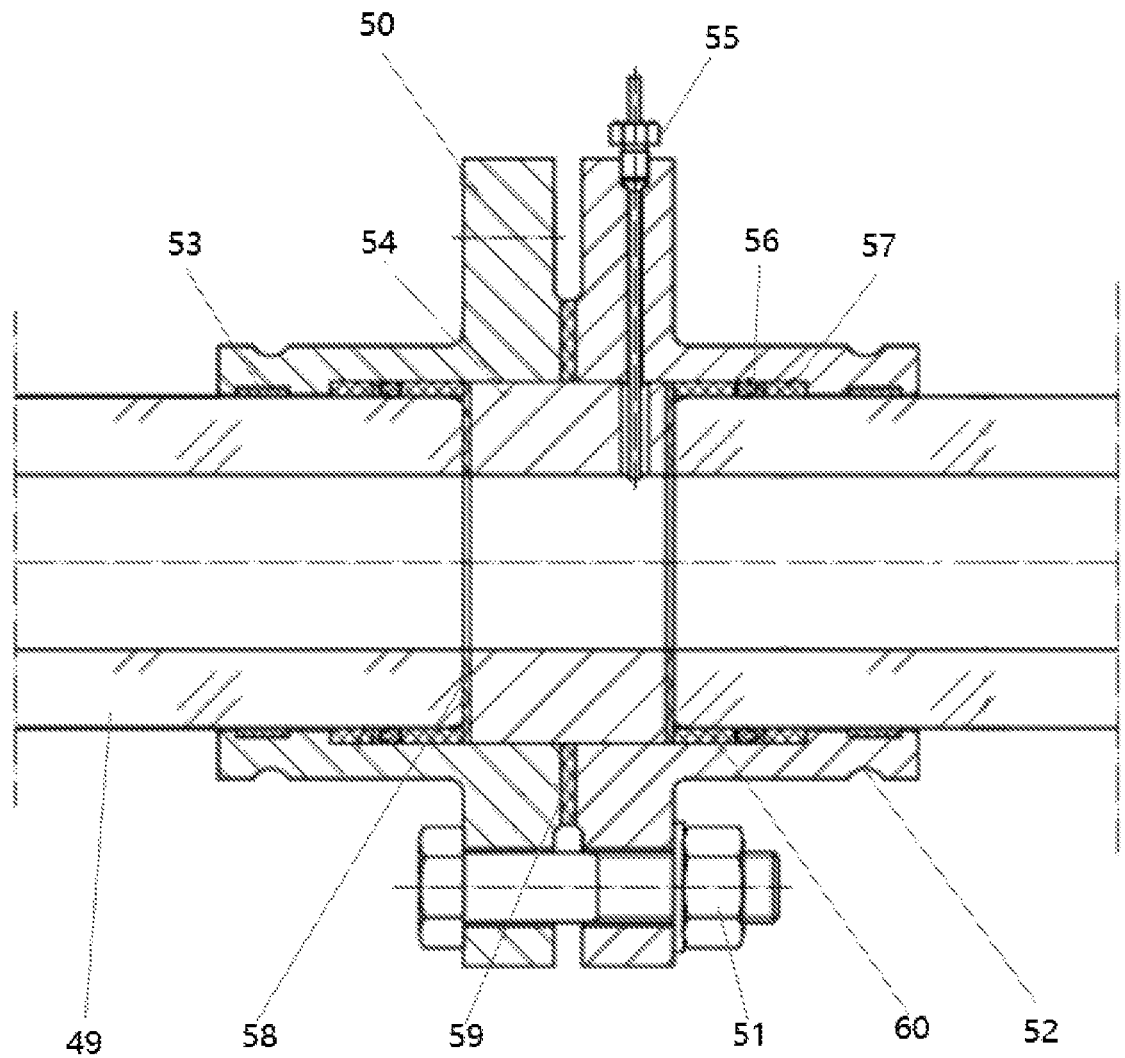
FIG. 5 is a structural diagram of the visual pipe connection way of the data acquisition system in the fully visual flow loop system for studying hydrate blockage in the present invention.

The first pipeline, the second pipeline, the third pipeline and the fourth pipeline are all formed by connecting a plurality of organic glass straight pipes 4. Two adjacent organic glass straight pipes 4 are connected through a connecting flange 9, a first pressure sensor 10 and a temperature sensor 11 are arranged on the connecting flange 9, and a pressure sensor 10 and a temperature sensor 11 are arranged on the connecting flange 9; and a visual window 6 is preferably arranged on a stainless steel bent pipe 5. The stainless steel bent pipes 5 and the organic glass straight pipes 4 in a preferred embodiment are all pressure-proof corrosion-resistant pipes and are made of high-transparency materials, and working pressure range is 0.1 MPa-5 MPa; an acoustic wave monitor 19, a gate valve 7 and a ball valve 8 are arranged on the first pipeline, the acoustic wave monitor 19 is used for acoustic wave detection of hydrate blockage, and the hydrate formation condition in different restricted areas can be simulated by controlling the opening degree of the ball valve 8. The single screw pump 16 can realize two-phase mixed transportation of large gas and liquid flow under certain pressure without crushing formed hydrate particles, the preferred maximum flow is about 25 m$^3$/h, and the air content range is preferably about 0-40%; and the single screw pump 16 and the mass flowmeter 13 can provide a circulating flow process for the fully visual pipeline system. For the following, see FIG. 5: one end of each visual pipe 49 stretches into the sealing flanges A 50, support rings 53, check rings 57, O-rings A 56 and distance rings 60 installed between the visual pipes 49 and the sealing flanges A 50 in order from inside to outside; flange plates of the two sealing flanges A 50 are fixed and abutted through bolts 51, a sealing gasket 59 is placed between the flange plates of the two sealing flanges A 50, a distance bush 54 is placed between the visual pipes 49 respectively stretching into the two sealing flanges A 50, and washers A 58 are installed between the distance bush 54 and the visual pipes 49; and sensors 55 are placed in sensor interfaces arranged on the sealing flanges A 50, and the pipeline is entirely fixed on the support through U-shaped clamp slot 52.

The fully visual pipeline system is arranged in the stepping low-temperature thermostatic chamber 3. A heat exchanger 1 and a methane concentration sensor 2 are arranged at one side of the stepping low-temperature thermostatic chamber 3, and the heat exchanger 1, the methane concentration sensor 2 and the stepping low-temperature thermostatic chamber 3 form a temperature control system. When the fully visual pipeline system needs refrigeration, the heat exchanger 1 starts to refrigerate, a temperature sensor 11 in the stepping low-temperature thermostatic chamber 3 can provide feedback and adjust temperature in real-time, and meanwhile, the methane concentration sensor 2 can realize the methane leakage alarm function. The working temperature range provided by the stepping low-temperature thermostatic chamber 3 is about −20° C. to 40°

C., the temperature control precision is ±0.5° C., and the refrigeration rate for reducing the temperature of the stepping low-temperature thermostatic chamber 3 from normal temperature (preferably about 20° C.) to about −20° C. within one hour can be realized.

The solution injection system includes a first solution tank 29 and a second solution tank 30, the first solution tank 29 communicates with the single screw pump 16 through a first solution conveying pipe, the second solution tank 30 communicates with the single screw pump 16 through a second solution conveying pipe, and the second solution tank 30 communicates with the second injection pipeline 39 through a pipeline. A first reciprocating pump 25, a pressure sensor 10 and a liquid flowmeter 40 are arranged on the first solution conveying pipe, and a second reciprocating pump 26 and a pressure sensor 10 are arranged on the second solution conveying pipe; the first solution tank 29 is a water solution tank and is made of stainless steel; the second solution tank 30 is a solution tank for chemical agents and corrosive liquids and is made of glass fiber reinforced plastics (GFRP). The solution injection system further includes a vacuum pump 27 connected to the first injection pipeline 18, and a pressure sensor 10 and a valve are arranged on the pipeline between the vacuum pump 27 and the first injection pipeline 18.

The pressure stabilizing and gas injection system includes a buffering and pressure stabilizing tank 31, a first gas booster pump 42 and an experimental gas cylinder group successively communicating with each other, where the buffering and pressure stabilizing tank 31 communicates with the second injection pipeline 39, a check valve 37, a gas flowmeter 41, a gas filter 47 and a second pneumatic valve 36 arranged on the pipeline between the buffering and pressure stabilizing tank 31 and the second injection pipeline 39, and the gas flowmeter 41 and the second pneumatic valve 36 are connected in series and then are connected with the gas filter 47 in parallel; an air compressor 28 is connected to the first gas booster pump 42, and the check valve 37 can prevent gas backflow; 40 L carbon fiber wrapped gas cylinders are selected for the experimental gas cylinder group 32, the standard pressure is 13.5 MPa, and the gas cylinders are connected in series and share one pressure reducing valve; and the volume of the buffering and pressure stabilizing tank 31 is designed to be 100 L and can meet gas supply needs for one experiment under the pressure of 20 MPa, and the tank body is made of high-strength steel.

The separation and collection system includes a natural gas collection tank 33 communicating with the second injection pipeline 39, an outlet of the natural gas collection tank 33 is divided into two conveying pipelines through a tee joint: a hand shutoff valve 35 and a gas-liquid separator 43 are connected to one conveying pipeline, a second gas booster pump 48 is connected behind the gas-liquid separator 43, and the other end of the second gas booster pump 48 communicates with the experimental gas cylinder group 32; and the other conveying pipeline is connected with a burner 44 through a pressure regulating valve 34, and the burner 44 is controlled by an igniter 46 connected with the burner 44, where the gas-liquid separator 43 can realize gas-liquid separation of water particles with precision of about ≤1.0 micrometer (μm).

The back pressure control system includes a back pressure regulating valve 38, a pressure sensor 10 and a hand shutoff valve 35 arranged on the pipeline between the natural gas collection tank 33 and the second injection pipeline 39. The withstanding pressure of the back pressure regulating valve 38 is 25 MPa, the pressure regulating range is 0-10 MPa, and the control precision is 0.1 MPa. The working process of the back pressure control system is as follows: when the experimental system needs stable outlet flow state, the hand shutoff valve 35 connected in front of the back pressure regulating valve 38 is opened, the equipment system pressure is regulated through the connected pressure sensors 10 and data acquisition system 15 and can be set according to experimental requirements.

The data acquisition system 15 includes a plurality of CCD cameras 14 arranged between the first pipeline, the second pipeline, the third pipeline and the fourth pipeline, all the above sensors and a computer electrically connected with the CCD cameras 14, all the above sensors, the liquid flowmeter 40, the mass flowmeter 13, and the like, respectively; and the CCD cameras 14 are respectively located in each organic glass straight pipe 4 and visual window 6. The data acquisition system 15 collects images in real-time through the CCD cameras 14; and the data acquisition system 15 collects data collected by all sensors in a centralized way and integrates and analyzes the image information collected by the CCD cameras 14 and the data monitored by all sensors.

The working process of the fully visual flow loop system for studying hydrate blockage in a preferred embodiment is as follows:

First, injecting a solution: starting the vacuum pump 27 to vacuumize the fully visual pipeline system, respectively injecting an experimental preparation solution into the first solution tank 29 and the second solution tank 30, starting the first reciprocating pump 25 and the second reciprocating pump 26 to pump the experimental solution into the circulating system, feeding back the dosage of the experimental solution pumped into the circulating system to the computer through the pressure sensors 10 and the liquid flowmeter 40; when the experimental solution pumped into the circulating system reaches the required pressure and experimental dosage, closing the hand shutoff valve 35, and closing the first reciprocating pump 25 and the second reciprocating pump 26 to stop the solution injection process;

after the solution injection system finishes the experimental solution injection process, open the hand shutoff valve 35 connected with the experimental gas cylinder group 32, conveying natural gas to the first gas booster pump 42 connected with the air compressor 28, and after the natural gas goes through the boosting process, pumping the boosted gas into the buffering and pressure stabilizing tank 31 for storage; when the experiment needs to supply gas for the circulating system, regulating the intake pressure and the intake flow required for the experiment through the data acquisition system 15, conducting real-time intake regulation through the second pneumatic valve 36, and feeding back the intake flow and pressure information through the gas flowmeter 41 and the pressure sensors 10 connected with both ends of the second pneumatic valve 36;

then starting the single screw pump 16 so that the fully visual pipeline system starts to operate, after the flow is stabilized, starting the temperature control system, gradually reducing the environment temperature to the experimental temperature, and maintaining constant temperature. As the flow process continues, hydrate may be formed in the pipeline to block the pipeline. At the moment, the temperature sensors 11, the pressure sensors 10, the mass flowmeter 13 and the acoustic wave monitor 19 records the temperature, pressure, flow and acoustic wave signals, and the like, in real-time, the data acquisition system 15 collects and analyzes the data in real-time, and the real time image of the hydrate formation process can be obtained through the CCD cameras 14 and the data acquisition system 15. In the operating process of the fully visual pipeline system, when natural gas is consumed due to hydrate formation, the data acquisition system 15 can automatically regulate the second pneumatic valve 36 through pressure data fed back in real-time to ensure automatic constant-pressure supplement of natural gas, and the check valve 37 can prevent gas backflow.

When the experimental system needs stable outlet flow state, opening the hand shutoff valve 35 connected in front of the back pressure regulating valve 38, regulating the equipment system pressure through the connected pressure sensors 10 and data acquisition system 15, and setting according to experimental requirements. After the gas discharged from the experimental system passes through the back pressure control system, introducing the discharged gas into the natural gas collection tank 33, and reflecting the gas content information in the natural gas collection tank 33 in real-time through the connected gas flowmeter 41, pressure sensors 10 and natural gas concentration sensor 45. When the gas in the natural gas collection tank 33 reaches a certain content; (1) opening the hand shutoff valve 35, and pumping the gas into the pressure stabilizing and gas injection system through the gas-liquid separator 43 and after boosting by the second gas booster pump 48; (2) opening the hand shutoff valve 35 in front of the pressure regulating valve 34, and starting the igniter 46 to burn up excessive natural gas through the burner 44 so that the natural gas can be prevented from being discharged into the atmosphere to cause greenhouse effect.

The data acquisition system 15 integrates sensor information in all the other systems and gives real-time feedback in the working process to ensure reasonable and coordinated operation of all systems.

The advantages of the fully visual flow loop system for studying hydrate blockage in a preferred embodiment can be used for studying:

(1) The formation and agglomeration characteristics of natural gas hydrate in the pipeline:

Different conditions such as temperature, pressure, flow rate, gas-liquid ratio and chemical additives in the pipeline cause different formation time, formation rate, formation position and formation amount of hydrate in the pipeline. In a preferred embodiment, by controlling the above mentioned experimental conditions, the parameters such as temperature and pressure during hydrate formation are monitored in real-time and analyzed through the data acquisition and analysis system formed of the temperature sensors 11, the pressure sensors 10, the differential pressure sensor 12, the mass flowmeter 13, the acoustic wave monitor 19 and the data acquisition system 15, and the real-time images of the hydrate formation and blockage process can be obtained;

(2) Acoustic wave character analysis of natural gas hydrate blockage in the pipeline:

Because the acoustic wave monitor 19 is added into the pipeline of the system, by emitting acoustic wave signals, reflected signals in the hydrate blockage area are analyzed to predict and judge the position of the hydrate blockage area and the shape of hydrate blockage;

(3) Differential pressure model analysis during formation of natural gas hydrate in the pipeline:

When natural gas hydrate is formed and blocks the pipeline in the flow process, an enormous differential pressure change will occur in the pipeline, and the differential pressure sensor 12 connected with the loop system can analyze the hydrate blockage degree based on differential pressure signals;

(4) Natural gas hydrate formation and blockage character analysis in the blind zones and flow dead zones of branch pipeline:

The blind zones and flow dead zones in actual pipeline are easiest to have natural gas hydration formation and blockage, and the hydrate blockage characteristics in these areas can be effectively observed and analyzed through a deadleg 24 added on the fourth pipeline;

(5) Natural gas hydrate formation and blockage characteristics analysis in inclined pipeline state:

The gas conveying pipeline is usually laid submarine slopes so that the pipeline forms a certain angle with the horizontal plane. Therefore, the hydrate formation and blockage character of the pipeline in different angles of inclination can be studied through the fluctuating pipeline in a preferred embodiment;

(6) Hydrate deposition character analysis in the pipeline in quick shut-down and re-start conditions:

The actual pipeline shut-down and re-start conditions can be simulated by opening or closing the loop system formed of the mass flowmeter 13, the single screw pump 16, the first pneumatic valve 20 and the differential pressure sensor 12 in order to study the blockage and deposition character of natural gas hydrate in the pipeline in the shut-down and re-start conditions.

It should be noted that the terms "first" and "second" in the description of the present invention are only used for description purpose and cannot be understood to indicate or imply relative importance.

Several examples are used for illustration of the principles and implementation methods of the present invention. The description of preferred embodiments is used to help illustrate the method and its core principles of the present invention. In addition, those skilled in the art can make various modifications in terms of specific embodiments and scope of application in accordance with the teachings of the present invention. In conclusion, the content of this specification shall not be construed as a limitation to the invention.

PARTS LIST 1 heat exchanger
2 methane concentration sensor
3 stepping low-temperature thermostatic chamber
4 organic glass straight pipe
5 stainless steel bent pipe
6 visual window
7 gate valve
8 ball valve
9 connecting flange
10 pressure sensor
11 temperature sensor
12 differential pressure sensor
13 mass flowmeter
14 CCD camera
15 data acquisition system
16 single screw pump
17 drain valve
18 first injection pipeline
19 acoustic wave monitor
20 first pneumatic valve
21 connecting hose
22 chain block
23 movable base
24 deadleg
25 first reciprocating pump 26 second reciprocating pump
27 vacuum pump
28 air compressor
29 first solution tank
30 second solution tank
31 buffering and pressure stabilizing tank
32 experimental gas cylinder group
33 natural gas collection tank
34 pressure regulating valve
35 hand shutoff valve
36 second pneumatic valve
37 check valve
38 back pressure regulating valve
39 second injection pipeline
40 liquid flowmeter
41 gas flowmeter
42 first gas booster pump
43 gas-liquid separator
44 burner
45 natural gas concentration sensor
46 igniter
47 gas filter
48 second gas booster pump
49 visual pipe
50 sealing flange A
51 bolt
52 U-shaped clamp slot
53 support ring
54 distance bush
55 sensor
56 O-ring A
57 check ring
58 washer A
59 sealing gasket
60 distance ring
61 top cover flange
62 protective pipe/fixed support
63 visual short pipe
64 O-ring B
65 U-ring
66 sealing flange B
67 spring pin assembly
68 locating rack
69 O-ring C
70 rotating joint
71 U-ring B
72 O-ring D
73 support belt
74 stainless steel tee pipe
75 locating plate
76 sealing flange C
77 washer B
78 first pipeline
79 second pipeline
80 third pipeline
81 fourth pipeline

LISTING OF ACRONYMS AND ABBREVIATIONS

° C. degrees Celsius
CCD charge-coupled device
GFRP glass fiber reinforced plastics
h hour
$m^3$ cubic meters
mPA megapascal
μm micrometer

What is claimed is:

1. A fully visual flow loop system for studying hydrate blockage, comprising a fully visual pipeline system, a solution injection system, a separation and collection system and a data acquisition system; wherein the fully visual pipeline system comprises a single screw pump and a first pipeline, a second pipeline, a third pipeline and a fourth pipeline connected successively in an end-to-end way, wherein the single screw pump is connected between the first pipeline and the fourth pipeline from the four pipelines, the first pipeline, the second pipeline, the third pipeline and the fourth pipeline are transparent to light, a plurality of CCD cameras are arranged among the first pipeline, the second pipeline, the third pipeline and the fourth pipeline, the fully visual pipeline system is arranged in a stepping low-temperature thermostatic chamber, and a heat exchanger is arranged at one side of the stepping low-temperature thermostatic chamber;

the solution injection system comprises a first solution tank and a second solution tank, wherein the first solution tank communicates with the single screw pump through a first solution conveying pipe, the second solution tank communicates with the single screw pump through a second solution conveying pipe, reciprocating pumps are arranged on the first solution tank and the second solution tank respectively, and a liquid flowmeter is also arranged on the first solution conveying pipe;

the separation and collection system comprises a natural gas collection tank connected with the fully visual pipeline system, wherein a gas-liquid separator and a burner are connected to an outlet of the natural gas collection tank;

the data acquisition system comprises pressure sensors arranged on the first solution conveying pipe, the second solution conveying pipe, the first pipeline, the second pipeline, the third pipeline and the fourth pipeline, temperature sensors arranged on the first pipeline, the second pipeline, the third pipeline and the fourth pipeline, a plurality of CCD cameras arranged between the first pipeline, the second pipeline, the third pipeline and the fourth pipeline, and a computer electrically connected with the CCD cameras, the pressure sensors and the temperature sensors respectively.

2. The fully visual flow loop system for studying hydrate blockage according to claim 1, wherein the first pipeline, the second pipeline, the third pipeline and the fourth pipeline are arranged horizontally and successively in parallel; the first pipeline, the second pipeline, the third pipeline and the fourth pipeline are connected successively through stainless steel bent pipes, the first pipeline also communicates with an inlet of the single screw pump through a first injection pipeline, the fourth pipeline also communicates with an outlet of the single screw pump through a second injection pipeline, a mass flowmeter is connected to the outlet of the single screw pump, the first injection pipeline is connected with the second injection pipeline through a connecting pipe, and a differential pressure sensor and a first pneumatic valve are arranged on the connecting pipe; the first pipeline, the second pipeline, the third pipeline and the fourth pipeline are all formed by connecting a plurality of organic glass straight pipes; the stainless steel bent pipes and the organic glass straight pipes are all made of high-transparency materials; and an acoustic wave monitor, a gate valve and a ball valve are arranged on the first pipeline.

3. The fully visual flow loop system for studying hydrate blockage according to claim 2, wherein one end of each visual pipe stretches into sealing flanges A, and support rings, check rings, O-rings A and distance rings are installed between the visual pipes and the sealing flanges A in order from inside to outside; flange plates of the sealing flanges A are fixed and abutted through bolts, a sealing gasket is placed between the flange plates of the sealing flanges, a distance bush is placed between the visual pipes respectively stretching into the sealing flanges A, and washers A are installed between the distance bush and the visual pipes; and sensors are placed in sensor interfaces arranged on the sealing flanges A, and the pipeline is entirely fixed on the support through U-shaped clamp slot.

4. The fully visual flow loop system for studying hydrate blockage according to claim 2, wherein the second pipeline and the third pipeline are both laid on a movable base, wherein one end of the movable base is rotatably connected to the ground, and the other end of the movable base can be lifted up through a chain block.

5. The fully visual flow loop system for studying hydrate blockage according to claim 2, wherein the solution injection system further comprises a vacuum pump connected to the first injection pipeline, wherein a valve and a pressure sensor electrically connected with the computer are arranged on the pipeline between the vacuum pump and the first injection pipeline.

6. The fully visual flow loop system for studying hydrate blockage according to claim 2, wherein a back pressure control system is arranged between the natural gas collection tank and the fully visual pipeline, wherein the back pressure control system comprises a back pressure regulating valve and a hand shutoff valve arranged between the natural gas collection tank and the fully visual pipeline as well as a pressure sensor connected with the computer.

7. The fully visual flow loop system for studying hydrate blockage according to claim 2, further comprising a pressure stabilizing and gas injection system, the pressure stabilizing and gas injection system comprises a buffering and pressure stabilizing tank, a first gas booster pump and an experimental gas cylinder group successively communicating with each other, the buffering and pressure stabilizing tank communicates with the second injection pipeline, a check valve, a gas flowmeter, a gas filter and a second pneumatic valve are arranged on the pipeline between the buffering and pressure stabilizing tank and the second injection pipeline, and the gas flowmeter and the second pneumatic valve is connected with the gas filter in parallel; and the gas-liquid separator communicates with one end of a second gas booster pump, and the other end of the gas booster pump communicates with the natural gas collection tank.

8. The fully visual flow loop system for studying hydrate blockage according to claim 2, wherein a deadleg is arranged on the fourth pipeline.

9. The fully visual flow loop system for studying hydrate blockage according to claim 2, wherein visual windows are arranged in all of the stainless steel bent pipes, and a drain valve is arranged on one of the stainless steel bent pipes.

10. The fully visual flow loop system for studying hydrate blockage according to claim 3, wherein the solution injection system further comprises a vacuum pump connected to the first injection pipeline, wherein a valve and a pressure sensor electrically connected with the computer are arranged on the pipeline between the vacuum pump and the first injection pipeline.

11. The fully visual flow loop system for studying hydrate blockage according to claim 3, wherein a back pressure control system is arranged between the natural gas collection tank and the fully visual pipeline, wherein the back pressure control system comprises a back pressure regulating valve and a hand shutoff valve arranged between the natural gas collection tank and the fully visual pipeline as well as a pressure sensor connected with the computer.

12. The fully visual flow loop system for studying hydrate blockage according to claim 3, further comprising a pressure stabilizing and gas injection system, the pressure stabilizing and gas injection system comprises a buffering and pressure stabilizing tank, a first gas booster pump and an experimental gas cylinder group successively communicating with each other, the buffering and pressure stabilizing tank communicates with the second injection pipeline, a check valve, a gas flowmeter, a gas filter and a second pneumatic valve are arranged on the pipeline between the buffering and pressure stabilizing tank and the second injection pipeline, and the gas flowmeter and the second pneumatic valve is connected with the gas filter in parallel; and the gas-liquid separator communicates with one end of a second gas booster pump, and the other end of the gas booster pump communicates with the natural gas collection tank.

13. The fully visual flow loop system for studying hydrate blockage according to claim 3, wherein a deadleg is arranged on the fourth pipeline.

14. The fully visual flow loop system for studying hydrate blockage according to claim 4, wherein the solution injection system further comprises a vacuum pump connected to the first injection pipeline, wherein a valve and a pressure sensor electrically connected with the computer are arranged on the pipeline between the vacuum pump and the first injection pipeline.

15. The fully visual flow loop system for studying hydrate blockage according to claim 4, wherein a back pressure control system is arranged between the natural gas collection tank and the fully visual pipeline, wherein the back pressure control system comprises a back pressure regulating valve and a hand shutoff valve arranged between the natural gas collection tank and the fully visual pipeline as well as a pressure sensor connected with the computer.

16. The fully visual flow loop system for studying hydrate blockage according to claim 4, further comprising a pressure stabilizing and gas injection system, the pressure stabilizing and gas injection system comprises a buffering and pressure stabilizing tank, a first gas booster pump and an experimental gas cylinder group successively communicating with each other, the buffering and pressure stabilizing tank communicates with the second injection pipeline, a check valve, a gas flowmeter, a gas filter and a second pneumatic valve are arranged on the pipeline between the buffering and pressure stabilizing tank and the second injection pipeline, and the gas flowmeter and the second pneumatic valve is connected with the gas filter in parallel; and the gas-liquid separator communicates with one end of a second gas booster pump, and the other end of the gas booster pump communicates with the natural gas collection tank.

17. The fully visual flow loop system for studying hydrate blockage according to claim 8, wherein the structure of the deadleg is as follows: one end of a stainless steel tee pipe is connected with a steel pipe sealing flange B, a rotating joint at the other end stretches into a sealing flange C, a support belt, an O-ring D and a U-ring B are arranged between the sealing flange C and the rotating joint, the sealing flange C is abutted with the steel pipe flange, and an O-ring C 69 is arranged on one face of the sealing flange C abutted with the steel pipe flange.

18. The fully visual flow loop system for studying hydrate blockage according to claim 17, wherein a locating plate is arranged on the stainless steel tee pipe, a plurality of locating holes are arranged in the locating plate, a locating rack is arranged on the sealing flange C, a spring pin assembly is arranged on the locating rack, and the spring pin assembly is connected with the locating plate and the locating rack through the locating holes.

19. The fully visual flow loop system for studying hydrate blockage according to claim 17, wherein both ends of a visual short pipe stretch into top cover flanges respectively, the top cover flange at the lower end is connected with a branch of the stainless steel tee pipe, a drain valve is arranged on the top cover flange at the upper end, the top cover flanges at both ends are permanently connected through a protective pipe, washers are arranged between the end faces of the visual short pipe and the top cover flanges, and O-rings B and U-rings A are arranged between the outer wall of the visual short pipe and the top cover flanges.

20. The fully visual flow loop system for studying hydrate blockage according to claim 1, wherein a methane concentration sensor electrically connected with the computer is also arranged at one side of the stepping low-temperature thermostatic chamber.

* * * * *